US012702415B2

(12) United States Patent
Tien et al.

(10) Patent No.: US 12,702,415 B2
(45) Date of Patent: Aug. 11, 2026

(54) APPARATUS AND METHODS FOR REMOVAL OF HEART VALVE LIGATION CLIP

(71) Applicant: Medtronic Vascular, Inc., Santa Rosa, CA (US)

(72) Inventors: Victoria Tien, Tustin, CA (US); Tasha Cheshko, Irvine, CA (US); Kshitija P. Garde, Fullerton, CA (US); Karl L. Olney, Irvine, CA (US); Luke Lehmann, Maple Grove, MN (US); Andrew Tiem-Yen Chang, Torrance, CA (US); Claudia See, Irvine, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1206 days.

(21) Appl. No.: 17/322,307

(22) Filed: May 17, 2021

(65) Prior Publication Data

US 2021/0401434 A1 Dec. 30, 2021

Related U.S. Application Data

(60) Provisional application No. 63/043,575, filed on Jun. 24, 2020.

(51) Int. Cl.

| | |
|---|---|
| ***A61B 17/076*** | (2006.01) |
| ***A61B 17/08*** | (2006.01) |
| *A61F 2/24* | (2006.01) |

(52) U.S. Cl.
CPC .......... *A61B 17/076* (2013.01); *A61B 17/083* (2013.01); *A61F 2/2454* (2013.01)

(58) Field of Classification Search
CPC ................ A61B 17/076; A61B 17/083; A61B 2017/00243; A61B 2017/00358; A61B 17/1285; A61B 17/128; A61B 17/122; A61B 17/1227; A61B 17/50; A61F 2/24–2466
See application file for complete search history.

(56) References Cited

U.S. PATENT DOCUMENTS

2007/0129737 A1 6/2007 Goldfarb et al.
2018/0008268 A1 1/2018 Khairkhahan
2019/0183571 A1* 6/2019 De Marchena ........ A61B 18/02
2020/0146690 A1 5/2020 Rothstein et al.
2020/0261107 A1* 8/2020 Cohen ............ A61B 17/320016

FOREIGN PATENT DOCUMENTS

EP 2760351 5/2018

* cited by examiner

*Primary Examiner* — Elizabeth Houston
(74) *Attorney, Agent, or Firm* — Medler Ferro Woodhouse & Mills PLLC

(57) ABSTRACT

Aspects of the disclosure include apparatuses for and methods of removing a ligation clip interconnecting two mitral valve leaflets. Methods can include providing a mitral valve having first and second valve leaflets interconnected with a ligation clip. The ligation clip includes a base supporting a first and second retaining arms each having an end opposite the base. The first and second valve leaflets are compressed between the first and second retaining arms. The methods further include physically separating the ligation clip from both of the first and second leaflets with the apparatus, which is configured to dislodge the first and second leaflets from the ligation clip. The apparatuses are further configured to withdraw the ligation clip from the patient along with the apparatus.

16 Claims, 18 Drawing Sheets

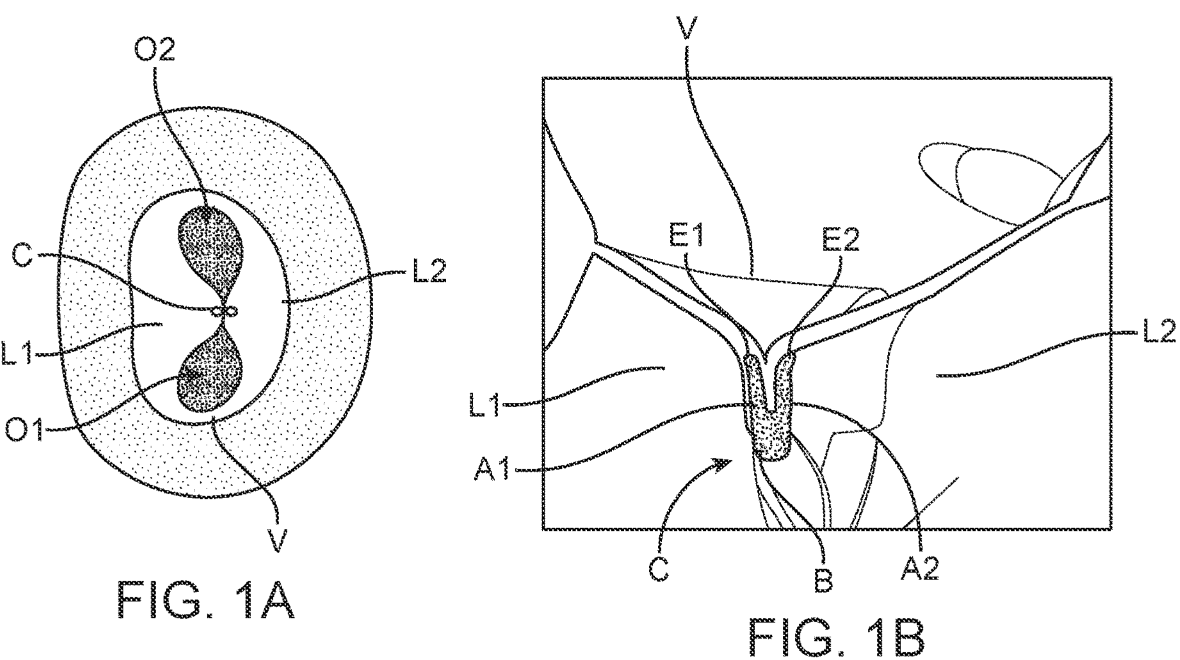
FIG. 1A
FIG. 1B
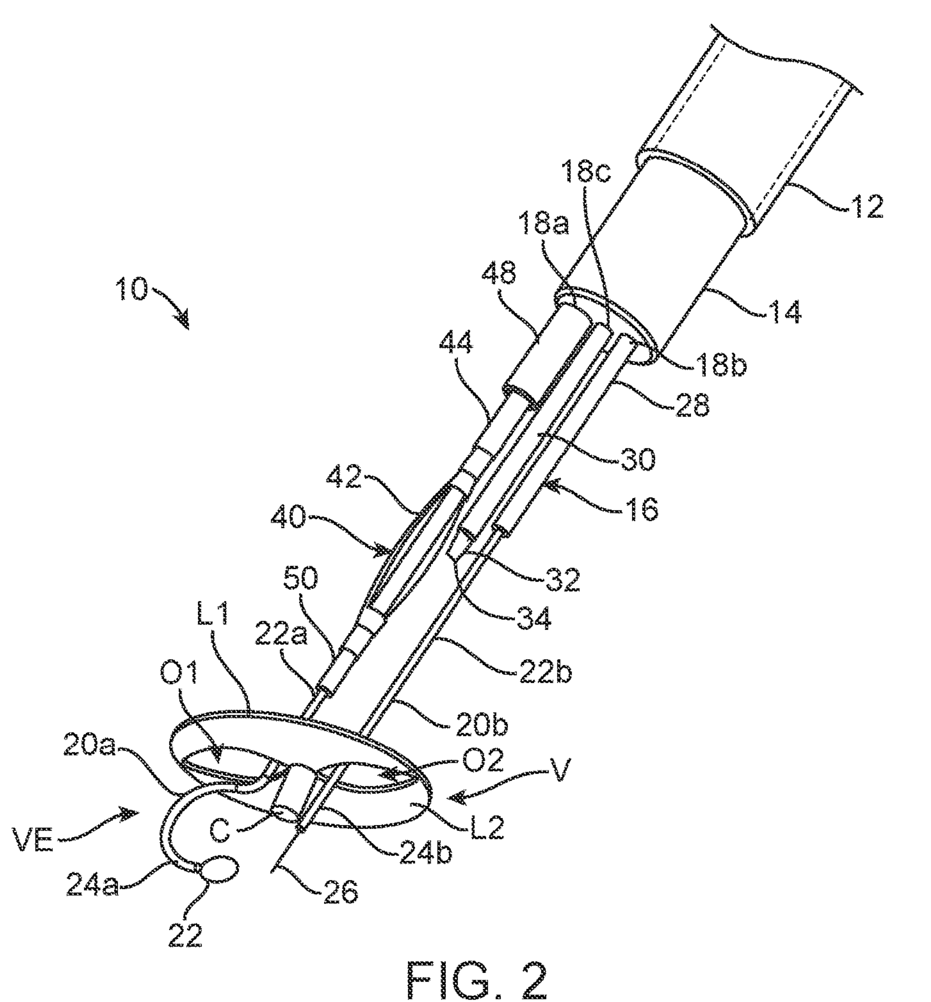
FIG. 2

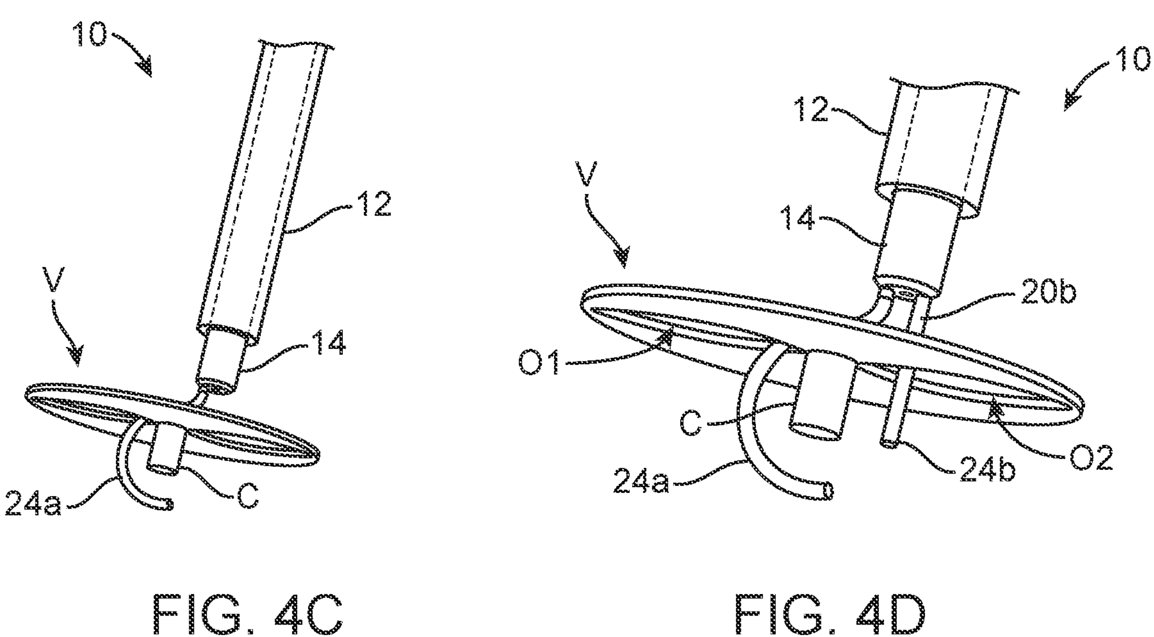
FIG. 4C
FIG. 4D
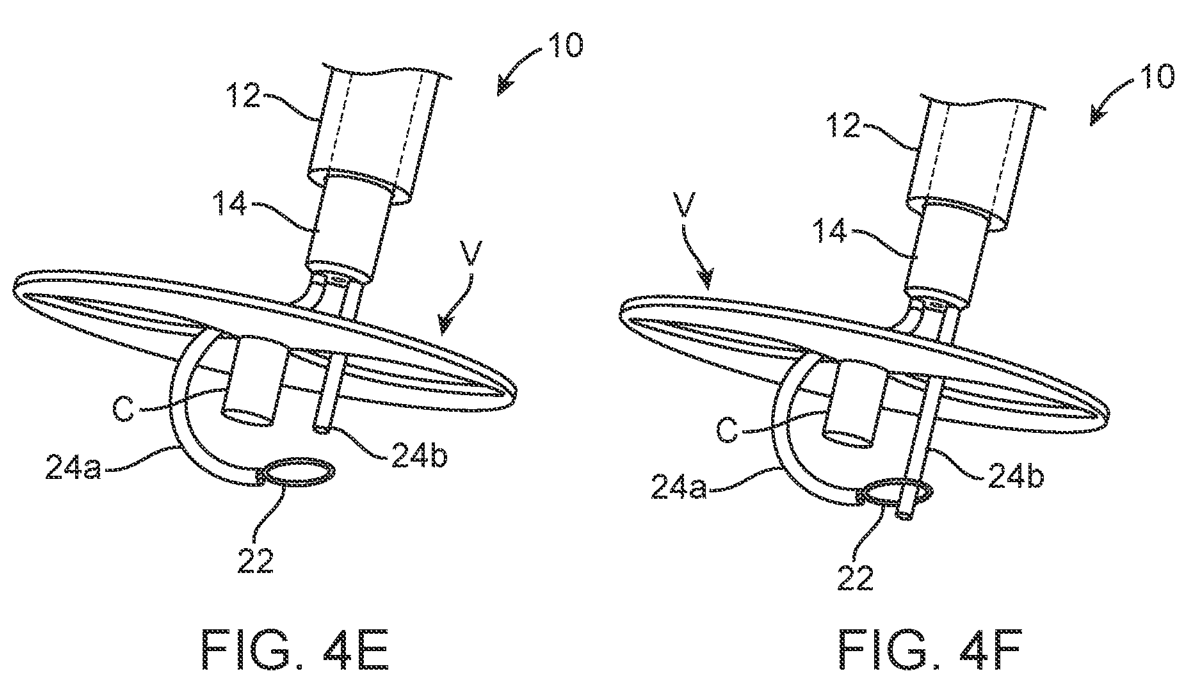
FIG. 4E
FIG. 4F

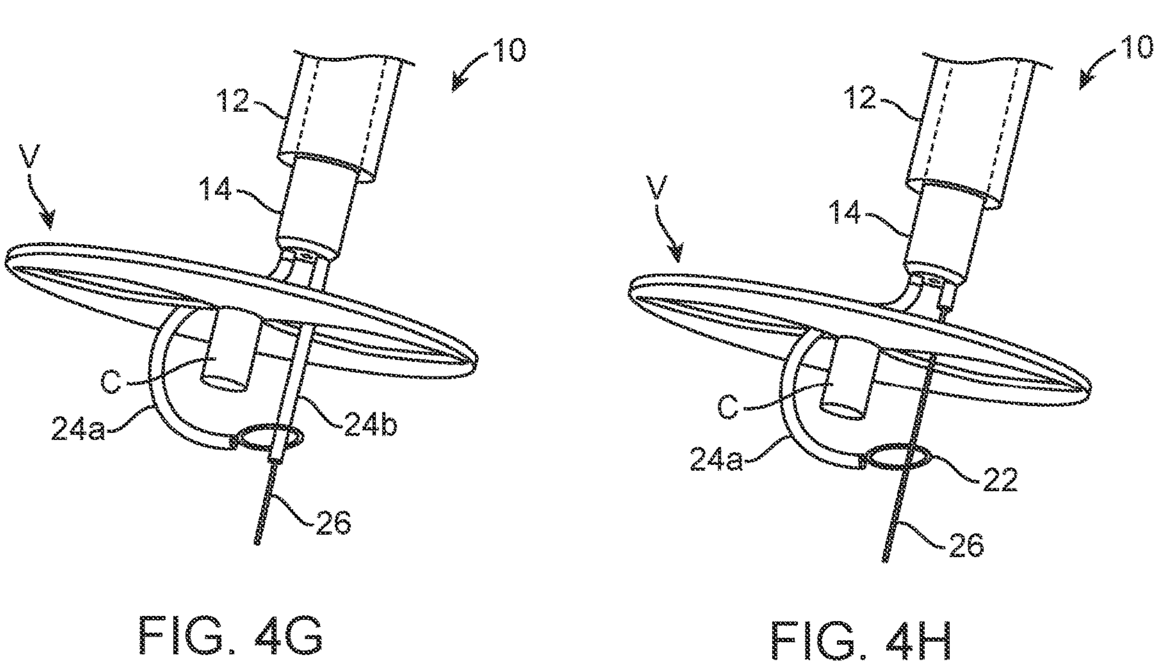
FIG. 4G
FIG. 4H
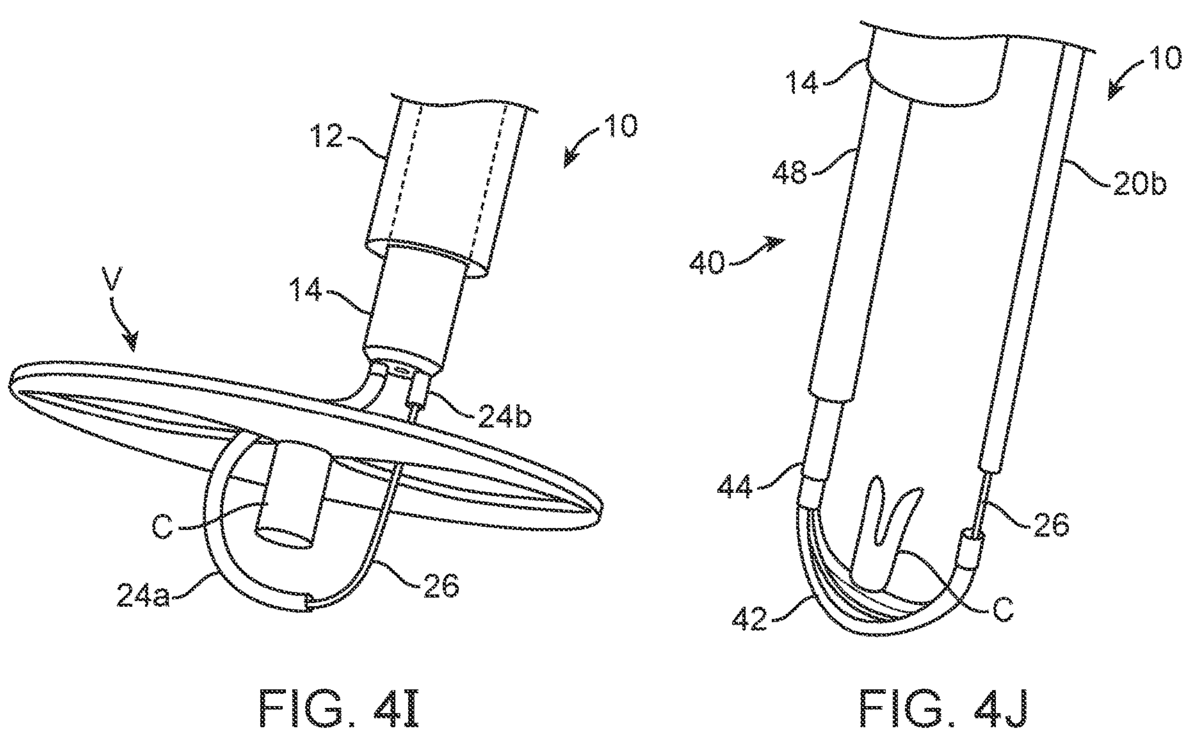
FIG. 4I
FIG. 4J

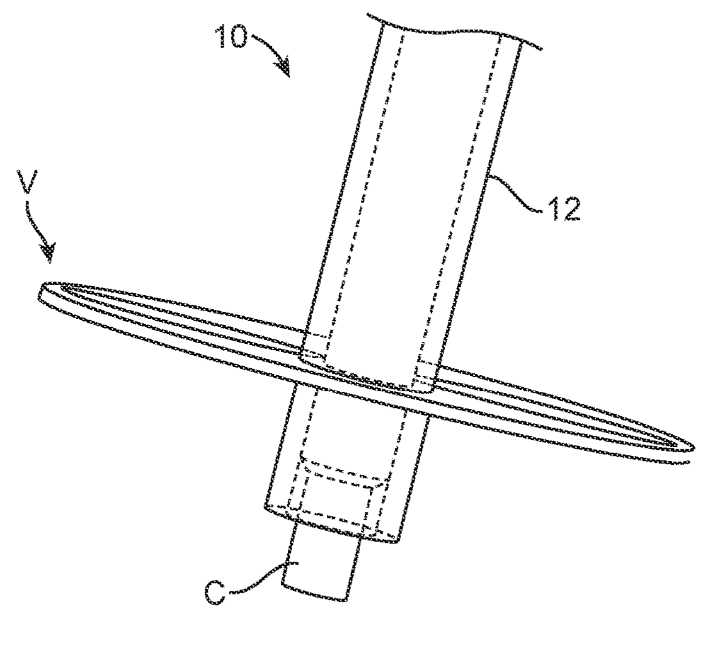
FIG. 6B
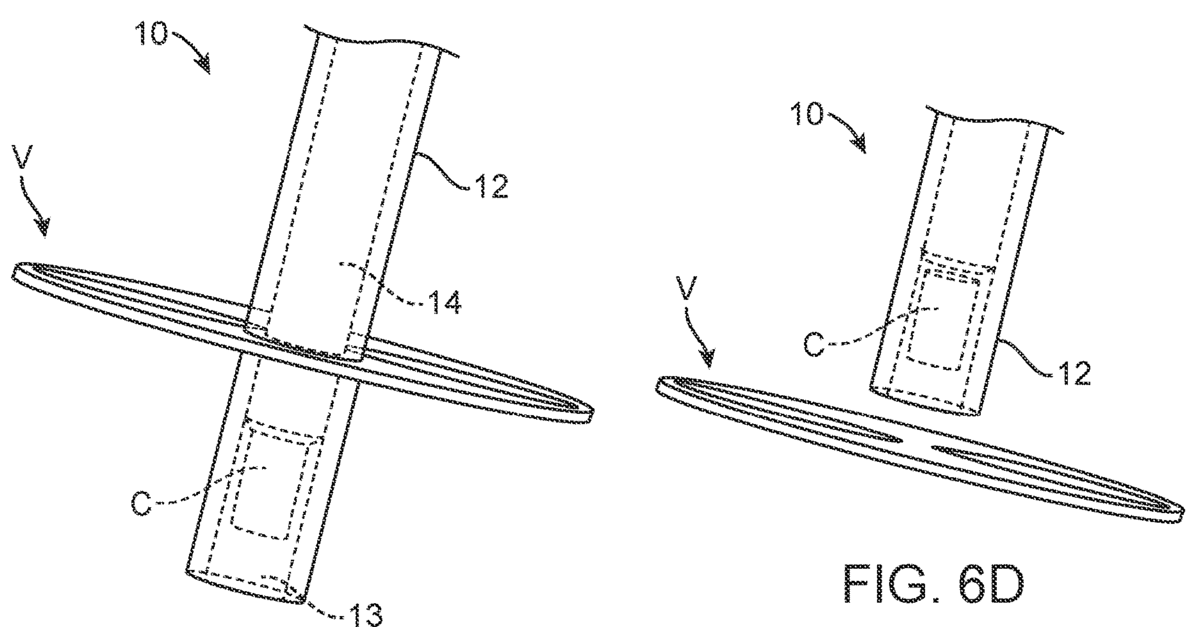
FIG. 6C
FIG. 6D

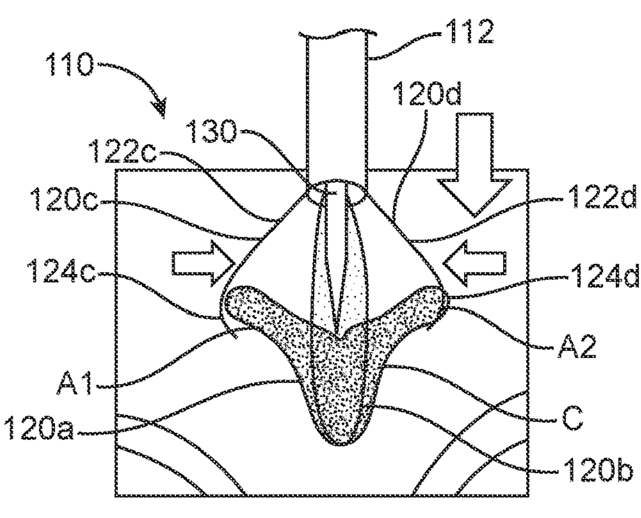
FIG. 9A
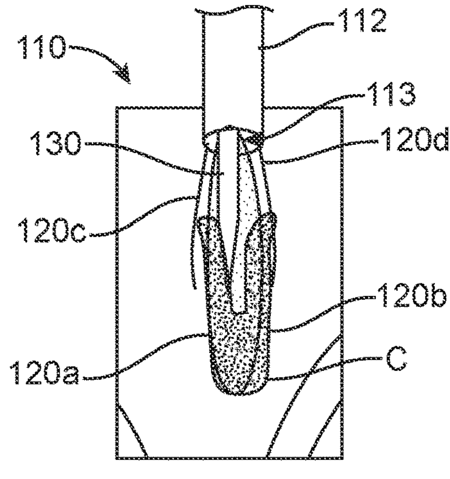
FIG. 9B
140
113
110
120d
112
130
120a
120b
120c
140
FIG. 10

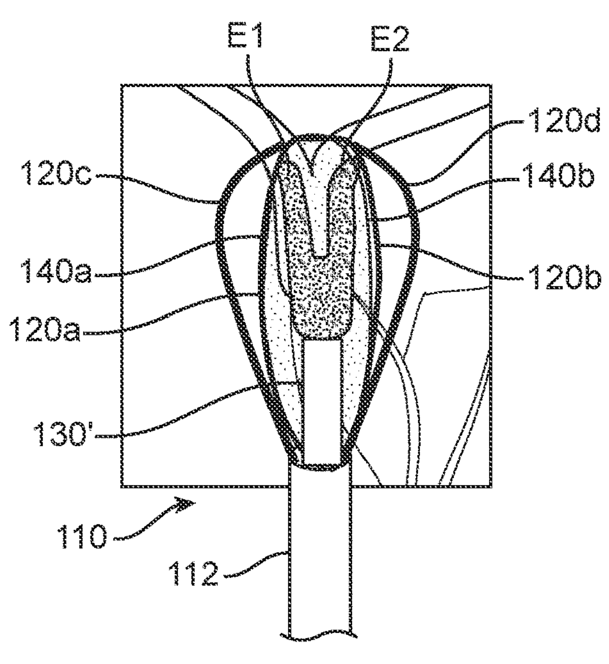
FIG. 11E
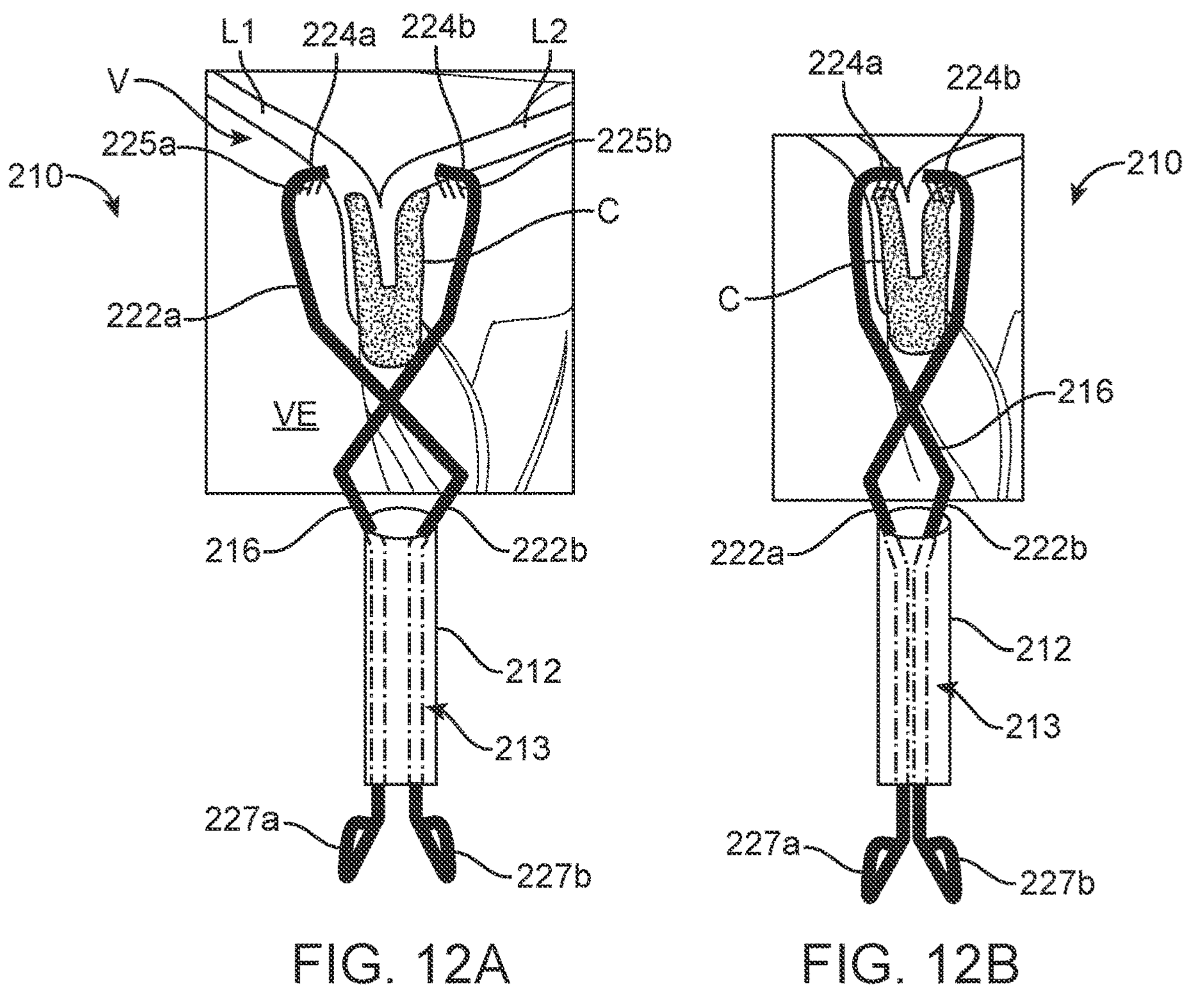
FIG. 12A
FIG. 12B

APPARATUS AND METHODS FOR REMOVAL OF HEART VALVE LIGATION CLIP

CROSS-REFERENCE TO RELATED APPLICATION

This Non-Provisional Patent Application claims the benefit of the filing date of U.S. Provisional Patent Application Ser. No. 63/043,575, filed Jun. 24, 2020, the entire teachings of which are incorporated herein by reference.

FIELD

The present technology is generally related to apparatuses for and methods for repairing a heart valve. Particularly, the present technology is generally related to apparatus for and methods for removing one or more ligation clips interconnecting two heart valve leaflets.

BACKGROUND

Various types of clips and surgical sutures (e.g., what is commonly known as an Alfieri stitch) are utilized to provide an edge-to-edge mitral valve repair. These techniques are used to reduce the regurgitation of a diseased mitral valve by clipping the anterior and posterior leaflets together in one or more locations to create a double orifice mimicking surgical edge-to-edge repair. When patients, are treated with a ligation clip or equivalent that are implanted with minimally invasive transcatheter techniques, those patients generally become ineligible to obtain transcatheter mitral prosthetic valve replacement in the future.

The present disclosure provides apparatuses and methods for removing one or more implanted ligation clips if clip placement is incorrect or to prepare the valve for implantation of a prosthetic valve if the one or more clips fail, are unsuccessful in resolving valve regurgitation, or there is re-occurrence of mitral regurgitation due to progressive annular dilatation, for example.

SUMMARY

The techniques of this disclosure generally relate to apparatuses for and methods of removing ligation clips joining heart valve leaflets. Such ligation clips may have been implanted for edge-to-edge heart valve repair to treat heart valve regurgitation. Should it be desired that the treated heart valve be replaced with a prosthetic heart valve or a clip be repositioned, aspects of the disclosure relate to apparatuses and methods for dislodging one or more ligation clips from heart valve leaflets. Various aspects of the disclosure relate to removal of one or more ligation clips in a non-destructive way while sparing native leaflets and chordae and destructive method by cutting leaflets around the clip in presence of native tissue ingrowth. Sparing sub-mitral valve leaflets has proven to be beneficial to reduce the progression or worsening of ventricle dilatation, which is the primary cause of functional mitral regurgitation. In various embodiments, the leaflets are preserved in that the leaflets are not cut or severed during the step of removing the one or more ligation clips. With various embodiments, each clip is dislodged from the leaflets and subsequently removed leaving the leaflet tissue intact after the clip is removed.

In one aspect, the present disclosure provides a clip removal apparatus for removing a tissue ligation clip that includes a pair of pivotably coupled arms or tissue engaging elements. In one example, the apparatus includes an outer, delivery sheath defining a lumen and terminating at a distal end. The apparatus further includes a wedge assembly having a wedge member, the wedge member slidably positioned coaxially with respect to the outer sheath, the wedge assembly including a delivery arrangement in which the wedge member is positioned within the outer sheath lumen and a deployed arrangement in which the wedge member is positioned outside the outer sheath lumen. The wedge member is configured to be advanced between the arms to pivot open the arms of the tissue ligation clip to be removed. The apparatus further includes a backstop assembly having a backstop member. The backstop member is coaxially positioned with respect to the outer sheath. The backstop assembly has a delivery arrangement in which the backstop member is positioned within the outer sheath lumen and a deployed arrangement in which the backstop member is positioned outside the outer sheath lumen, where the backstop member is configured to surround at least a portion of the tissue ligation clip to be removed while the wedge member is advanced between the arms of the tissue ligation clip.

In another aspect, the disclosure provides methods of removing a tissue ligation clip interconnecting two valve leaflets. For example, methods can include providing a mitral valve having first and second valve leaflets interconnected with a tissue ligation clip. The tissue ligation clip includes a base supporting first and second retaining arms or tissue engaging elements each having an end opposite the base. The first and second valve leaflets are compressed between the first and second arms. The methods further include physically separating the tissue ligation clip from both of the first and second leaflets with an apparatus configured to dislodge the first and second leaflets from the tissue ligation clip.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 1A is a top view of a mitral valve having a tissue ligation clip interconnecting two valve leaflets.

FIG. 1B is a cross-sectional view of FIG. 1A.

FIG. 2 is a partial, perspective view of an apparatus including a support assembly having first and second supports for dislodging and removing the tissue ligation clip.

FIGS. 4A-4J illustrate a method of the disclosure for dislodging the tissue ligation clip and retrieving the clip with the apparatus of FIGS. 2-3B.

FIGS. 6A-6D illustrate another method of dislodging the tissue ligation clip with the apparatus of FIGS. 2-3B.

FIGS. 9A-9B illustrate an alternate method of using the apparatus of FIGS. 7A-7E when the apparatus is further provided with graspers.

FIG. 10 is a cross sectional illustration of the alternate apparatus of FIGS. 9A-9B.

FIGS. 11A-11E illustrate an alternate method of using the apparatus of FIG. 10

FIG. 12A is a schematic illustration of an alternate apparatus in an open arrangement.

FIG. 12B is a schematic illustration of the apparatus of FIG. 12A in a closed arrangement.

DETAILED DESCRIPTION

Figure 3A:
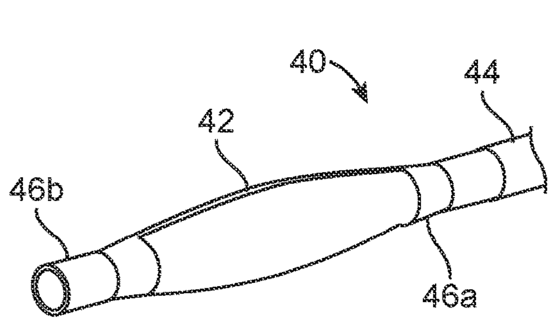
FIG. 3A is a perspective view of a backstop member of the support assembly in a compressed delivery arrangement.

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Referring to FIGS. 1A-1B, it is common to treat a diseased mitral valve V by securing anterior and posterior leaflets L1, L2 together in one or more locations with a ligation device C. This procedure results in the valve having first and second openings O1, O2. In one example, the ligation device C is a clip that includes a base B supporting two tissue engaging elements or arms A1, A2. The arms A1, A2, having respective terminal ends E1, E2, can be formed of a shape memory material and can be biased toward each other to effectively form a clamp. In other words, the arms A1, A2 are pivotal with respect to the base B and are biased to provide a compressive force on the leaflets L1, L2 to maintain the leaflets together and the clip C on the leaflets. The present disclosure provides numerous apparatuses and methods for removing one or more ligation clips from heart valve leaflets.

FIGS. 2-6 collectively illustrate an apparatus 10 configured to dislodge a ligation clip (e.g., clip C of FIGS. 1A-1B) from two heart valve leaflets (e.g., leaflets L1, L2). In this embodiment, the apparatus 10 includes an outer, delivery sheath, tube, or shaft 12 (partially shown) coaxially positioned around a middle delivery sheath, tube, or shaft 14. The middle delivery sheath 14 can maintain a support assembly 16. In one example, the middle delivery sheath 14 includes one or more lumens 18*a*, 18*b* in which first and second supports 20*a*, 20*b* of the support assembly 16 are slidably positioned. The supports 20*a*, 20*b* can be microcatheters each including a lumen (not visible). Each support 20*a*, 20*b* has an extension portion 22*a*, 22*b* connected to distal end portion 24*a*, 24*b*. The support assembly 16 has a delivery arrangement in which the distal end portions 24*a*, 24*b* of each of the first and second supports 20*a*, 20*b* are positioned within the respective lumen 18*a*, 18*b* and a deployed arrangement in which the distal end portions 24*a*, 24*b* of each of the first and second supports 20*a*, 20*b* are positioned outside of the respective lumen 18*a*, 18*b*. In one example, the distal end portion 24*a* of the first support 20*a* can be made of a shape memory material and configured to have a semicircular or curved hook shape in a natural arrangement as shown in FIG. 2. In one example, the distal end portion 24*a* of the first support 20*a* can be straightened in the delivery arrangement to fit within the respective lumen 18*a* of the middle delivery sheath 14.

Within the lumen of the first support 20*a* is a loop snare 22 that can include a shape memory wire or stiffened radiopaque suture, for example. The second support 20*b* can also be a microcatheter through which an elongate member 26 (e.g., suture or wire) can be maintained. Optionally, the second support 20*b* can include an outer support sheath 28 extending along at least a portion of the second support 20*b* between the second support and the middle delivery sheath 14.

The middle delivery sheath 14 additionally maintains a rigid wedge assembly 30 slidably positioned within a lumen 18*c*. In one embodiment, the wedge assembly 30 is coaxial with a center axis of the middle delivery sheath 14. As shown, the wedge assembly 30 can include a tapered wedge member 32 having a blunt tip 34 (see, in particular, FIGS. 2 and 5). For example, the wedge member 32 may include two, opposing tapered surfaces 36 (best shown in FIG. 5) that converge toward the blunt tip 34. In the illustrated example, the wedge assembly 30 is positioned between the first and second supports 20*a*, 20*b*, along a central axis of the middle delivery sheath 14.

Figure 3B:
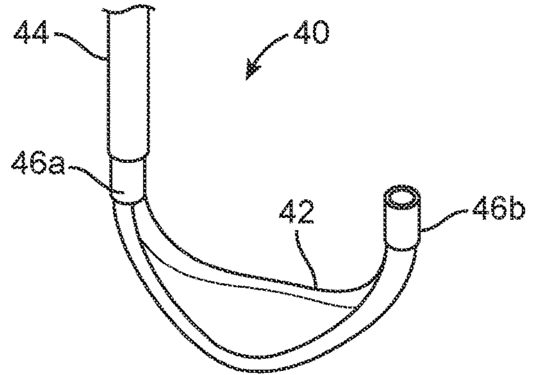
FIG. 3B is a perspective view of the backstop member of FIG. 3A in an expanded, deployed arrangement.

The first support 20*a* can be provided as part of a backstop assembly 40 that also includes a backstop member 42 slidably positioned on the first support 20*a*. The backstop member 42 provides a supportive surface for the wedge member 32 to be pressed against as will be discussed in further detail below. In one example, the backstop member 42 is secured to a backstop shaft 44 that is slidably positioned over the first support 20*a* at least partially within the lumen 18*a*. The backstop member 42 is configured to be selectively deployed from a compressed delivery arrangement (FIGS. 2, 3A) to an expanded deployed arrangement (FIGS. 3B, 4J). In various embodiments, the backstop member 42 is made of a mesh, such as a shape memory metal mesh (Nitinol braided mesh). The backstop member 42 is configured such that it can be elongated and reduced in profile for delivery and expanded to create a basket for supporting the wedge member 32 and the clip C. In this way, the backstop member 42 may span less than 360 degrees of the first support 20*a*. In one example, the backstop member 42 may span approximately 180 degrees (+/−5 degrees) of the first support 20*a*. In various embodiments, the backstop member 42 may be connected to the first support 20*a* at proximal and distal ends 46*a*, 46*b* of the backstop member 42. The backstop assembly 40 can further include a backstop shaft 44 provided to selectively compress the backstop member 42 to transition the backstop member 42 between the reduced and expanded profiles. In various embodiments the first support 20*a* can include a support tube 50 positioned over at least a portion of its length to support and reinforce the extension portion 22*a*.

Figure 4A:
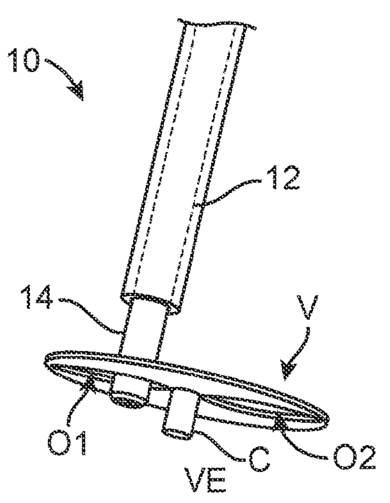
Figure 4B:
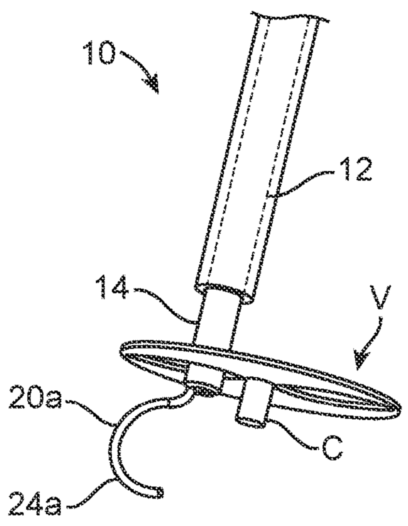
Figure 5:
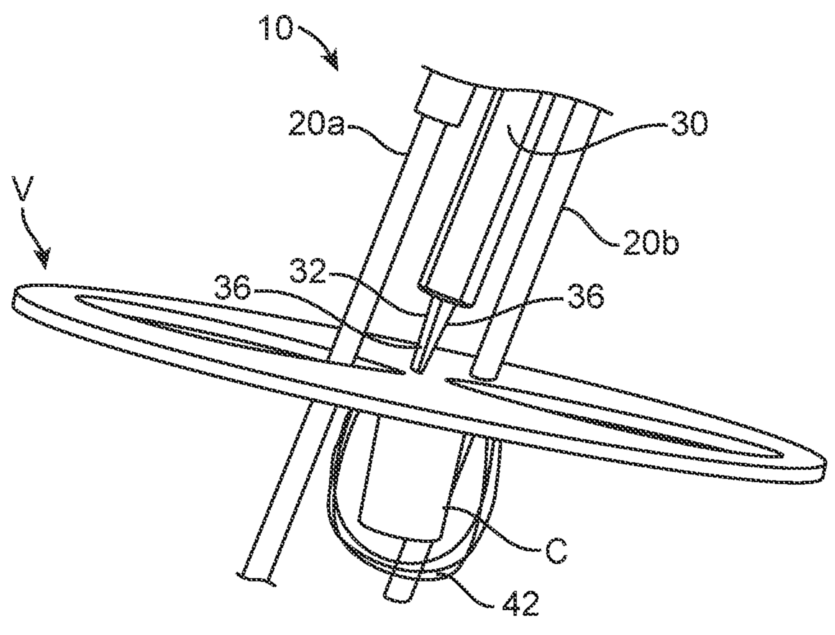
FIG. 5 illustrates one method of dislodging the tissue ligation clip with a wedge assembly of the apparatus of FIGS. 2-3B.

In one example of use, the apparatus 10 is delivered in the delivery arrangement via a patient's vasculature via transseptal approach to a heart valve to be treated, such as a mitral valve (FIG. 4A). In one example, as shown in FIGS. 1A-1B, the ligation clip C interconnects two leaflets L1, L2 such that the mitral valve V has first and second opening O1, O2 on opposing sides of the ligation clip C. A distal end of the middle delivery sheath 14 is positioned adjacent the first opening O1 and the first support 20*a* is inserted through the first opening O1 and into the ventricle VE. As the first support 20*a* is pushed out of the middle delivery sheath 14, the distal end portion 24*a* of the first support 20*a* naturally transitions to its natural arrangement (FIG. 4B). A distal end of the distal end portion 24*a* is positioned adjacent and underneath the base of the ligation clip C (FIGS. 4C-4D). Then, the loop snare 22 is advanced distally out of the first support 20*a* (FIG. 4E). The second support 20*b* is inserted through the second opening O2 of the mitral valve V and through the loop snare 22 (FIG. 4F). The elongate member 26 is then distally advanced out of the distal end portion 24*b* of the second support 20 and through the loop snare 22 (FIG. 4G). The second support 20*b* is then proximally withdrawn from the loop snare 22 leaving the elongate member 26 threaded through the loop snare 22 (FIG. 4H). The loop snare 22 is then proximally withdrawn, which pulls the elongate member 26 into the lumen of the first support 20*a* (FIG. 4I). Then, the backstop member 42 is distally advanced over the distal portion 24*a*, via the backstop assembly 40 or otherwise (FIG. 4J). In one example, as shown in FIG. 5, the backstop member 42 is deployed and advanced by pulling the backstop outer sheath 48 proximally until the backstop member 42 is exposed and then advancing the backstop shaft 44 distally along the first support 20*a* until the backstop member 42 is positioned underneath the ligation clip C. In an alternate method, the backstop sheath 48 may be positioned over the backstop member 42 until the backstop member 42 is inserted through the opening O1. In one example, the backstop member 42 is positioned to be aligned with a central axis of the outer delivery sheath 12. The wedge member 32 is then distally advanced from the middle delivery sheath 14 to a position between the arms A1, A2 of the clip C, adjacent the base B. As the wedge assembly 30 is distally advanced, the wedge member 32 pushes the base B distally, against the backstop member 42 to open arms A1, A2 and dislodge (e.g., push down) the ligation clip C from the leaflets L1, L2. It will be understood that in alternate examples, the first support 20*a* can be inserted through the second opening O2 and the second support 20*b* can be inserted through the first opening O1.

Figure 6A:
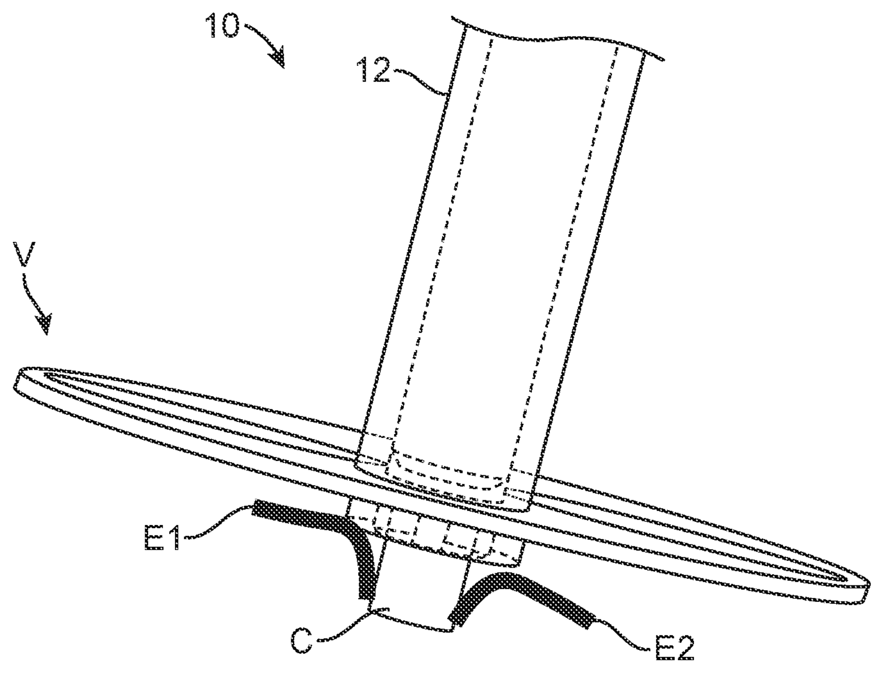

In the example of FIG. 6A, the wedge assembly is omitted (or provided but not utilized) and the distal end of the middle shaft 14 is instead distally advanced to engage and push the arms A1, A2 of the ligation clip C. This action deforms the arms A1, A2 of the clip approximately 90 degrees (+/−5 degrees) with respect to the base B. By pushing the arms A1, A2 away from the leaflets L1, L2, the ligation clip C is dislodged from the leaflets for removal of the clip.

In various embodiments, the outer delivery sheath 12 is advanced distally to encapsulate the ligation clip C within its lumen 13, distal to the middle shaft 14. See FIGS. 6B-6D, for example. Then the apparatus 10, including the clip C, is proximally withdrawn from the patient in the same manner as the apparatus was delivered.

Figure 7A:
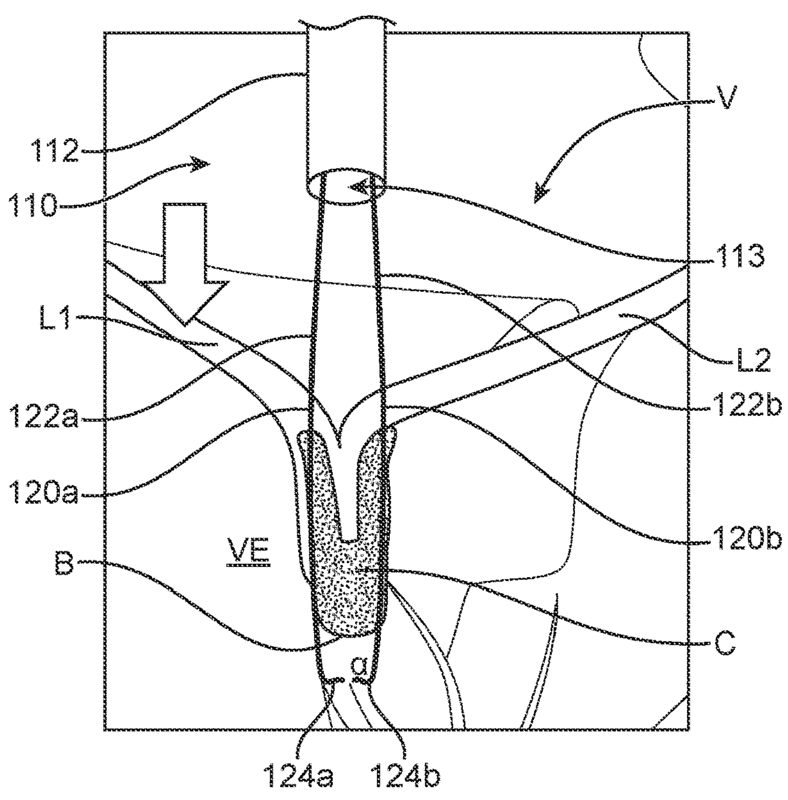
FIG. 7A is a schematic illustration of an alternate apparatus for dislodging and removing the tissue ligation clip in which first and second supports of a support assembly are deployed from an outer delivery sheath.
Figure 7B:
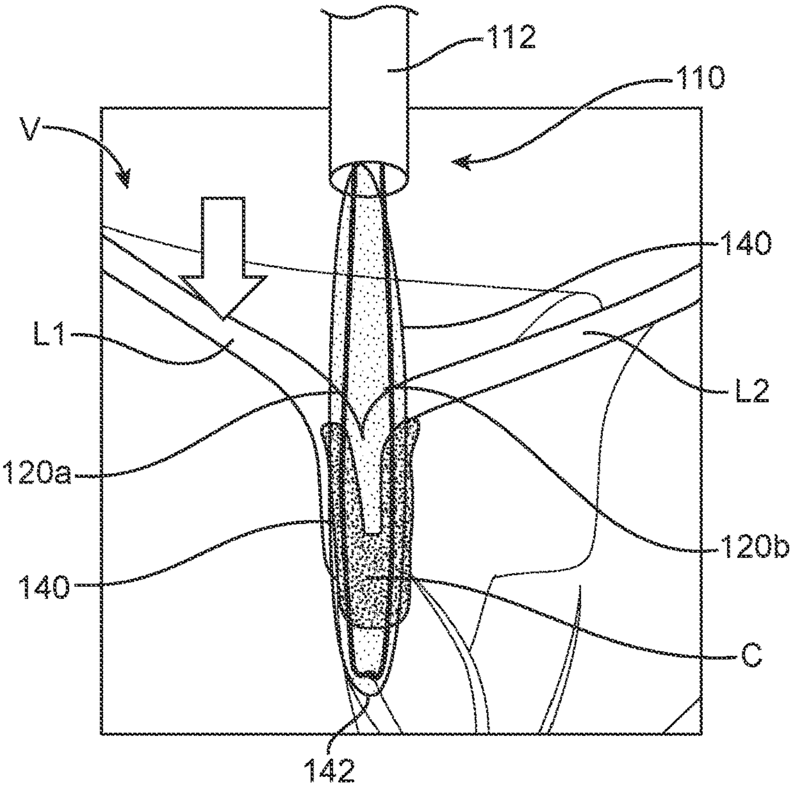
FIG. 7B is a schematic illustration of the apparatus of FIG. 7A in which backstop assemblies of the support assembly are deployed form the outer delivery sheath and over the first and second supports.
Figure 7C:
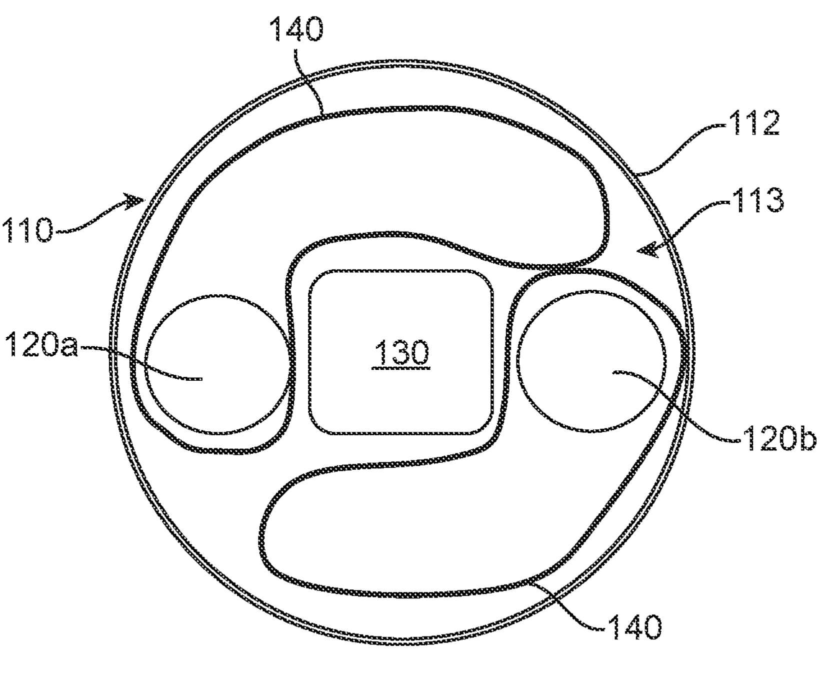
FIG. 7C is a cross-sectional view of the apparatus of FIGS. 7A-7B.
Figure 7D:
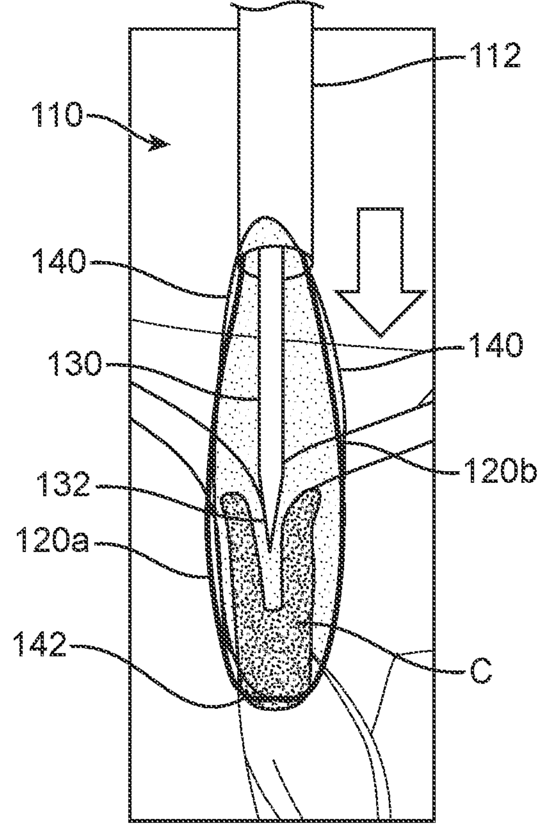
FIG. 7D is a schematic illustration of a wedge assembly distally advanced out of the outer delivery sheath and between arms of the tissue ligation clip.

Referring now in addition to FIGS. 7A-7D which collectively illustrate another apparatus 110 for dislodging the ligation clip C from leaflets L1, L2. In this embodiment, the apparatus 110 includes an outer delivery sheath 112 having a lumen 113. The outer delivery sheath 112 maintains a support assembly 116 including a plurality of supports 120*a*, 120*b*. In one example, the support assembly 116 includes two supports 120*a*, 120*b*. At least some of the supports 120*a*, 120*b* including an extension portion 122*a*, 122*b* and a distal end portion 124*a*, 124*b*. The distal end portions 124*a*, 124*b* can be angled with respect to the respective extension portion 122*a*, 122*b* in a normal arrangement. In one example, the angle α is approximately 90 degrees (+/−5 degrees). Each support 120*a*, 120*b* can be made of a shape memory material (e.g., Nitinol) so the support can be delivered to the ligation clip C in a linear configuration, positioned entirely within the lumen 113. Once distally advanced and freed from the confines of the outer delivery sheath 112, the supports 120*a*, 120*b* can automatically transition to their normal arrangements. As shown in FIG. 7D, at least two of the distal end portions 124*a*, 124*b* can collectively form a backstop member that can be positioned adjacent the base B of the ligation clip C, opposite the outer delivery sheath 112. In one example, at least one support 120*a*, 120*b* further includes slidable backstop assembly 140 (schematically shown) including a backstop member 142, which can optionally be configured similar to the backstop assembly 40 and/or backstop member 42 embodiment of FIGS. 2-6, As shown in FIGS. 7C-7D, the apparatus 110 further includes a wedge assembly 130 that can be configured similar to and operate similarly as compared to wedge assembly 30. The backstop member 142 can be provided to reinforce the clip C and wedge assembly 130 and essentially provides a basket for catching the ligation clip C once dislodged from the leaflets L1, L2. The wedge assembly 130 can include a wedge member 132 similar or identical to wedge member 32. In one example, the wedge member 132 is tapered or wedged shaped as disclosed with respect to the embodiment of FIGS. 2-6. The wedge member 132 can be maintained within the outer delivery sheath 112 and can be distally advanced between clip arms A1, A2 to dislodge the ligation clip C from the leaflets L1, L2 and at least partially into the basket formed by the backstop member 142. Once the arms A1, A2 of the clip C are forced outwardly, away from each other by the wedge member 132, the arms A1, A2 disengage from the leaflets L1, L2. Once disengaged and moved away from the leaflets L1, L2, the wedge member 132 can be proximally withdrawn and the clip arms A1, A2 will snap shut. The wedge member 132 and supports 120*a*, 120*b* can then be proximally withdrawn into the outer delivery sheath 112 with the ligation clip C in the same manner as the apparatus 110 was delivered.

Figure 8A:
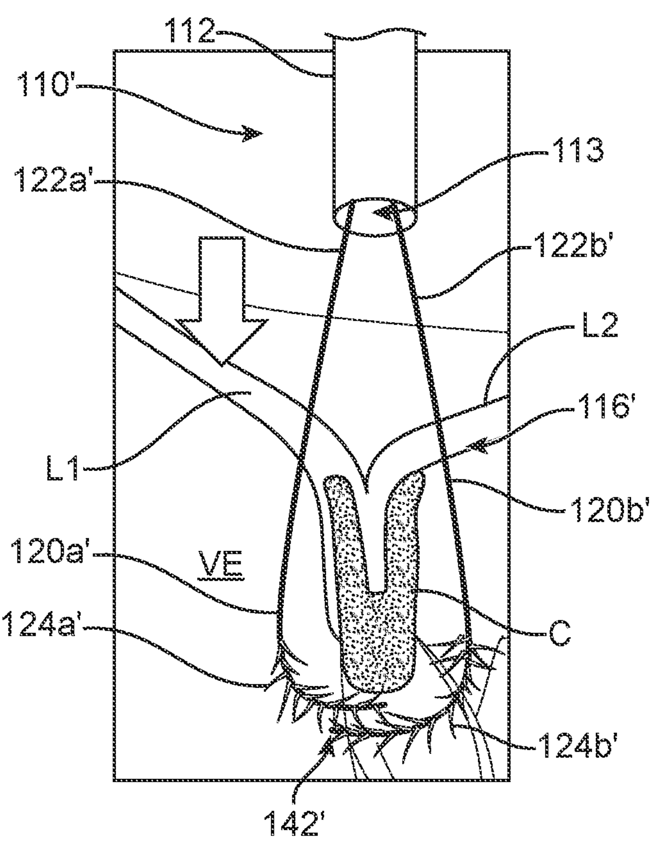
FIG. 8A is a schematic illustration of an alternate apparatus for dislodging the tissue ligation clip, the apparatus including a support assembly having first and second supports.
Figure 8B:
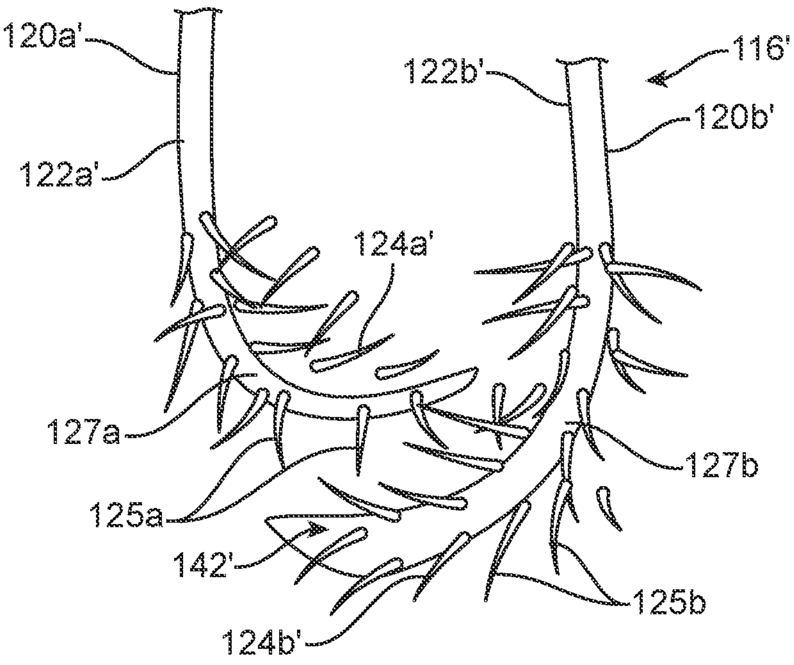
FIG. 8B is an enlarged view of distal end portions of the first and second supports of FIG. 8A.

As shown in FIGS. 8A-8B, an alternate apparatus 110' can include the outer delivery sheath 112 but one or more supports (i.e. a substitute for 120*a*, 120*b* of FIGS. 7A-7D) 120*a*', 120*b*' can be configured to have an extension portion 122*a*', 122*b*' and a distal end portion 124*a*', 124*b*' including a plurality of outwardly extending extensions 125*a*, 125*b* (generally referenced) that can flex with respect to a body 127*a*, 127*b* of the respective distal end portion 124*a*', 124*b*' and are adequately strong to enable functionality of backstop. When positioned outside of the lumen 113 of the outer delivery sheath 112, the extensions 125*a*, 125*b* are configured to at least partially overlap and intertwine to form a basket or backstop member 142' to further support the wedge assembly 130 (see also FIGS. 2 and 5, for example)

and catch the clip C. In one example, the extensions 125*a*, 125*b* are made of a shape memory or flexible material.

It is envisioned that the ligation clip arms A1, A2 may not necessarily snap shut, as expected. Therefore, the apparatus 110' can include two additional supports or graspers 120*c*, 120*d* slidably positioned in the outer delivery sheath 112. As shown in FIGS. 9A-10, the graspers 120*c*, 120*d* can be distally advanced and positioned at ends E1, E2 of the arms A1, A2. Each grasper 120*c*, 120*d* can be similarly configured to supports 120*a*, 120*b*. In one example, each grasper 120*c*, 120*d* includes and extension portion 122*c*, 122*d* and a distal end portion 124*c*, 124*d*. The distal end portions 124*c*, 124*d* of the supports 120*c*, 120*d* can be biased to be angled with respect to the respective end portion 122*c*, 122*d*. The distal end portions 124*c*, 124*d* can engage the ends E1, E2 of the arms A1, A2 and then be proximally withdrawn to urge the arms A1, A2 together (i.e. closed). Once the arms A1, A2 are closed, the clip C can be proximally pulled within the lumen 113 of the outer delivery sheath 112 with two or more supports 120*a-d* for removal from the patient.

Figure 11A:
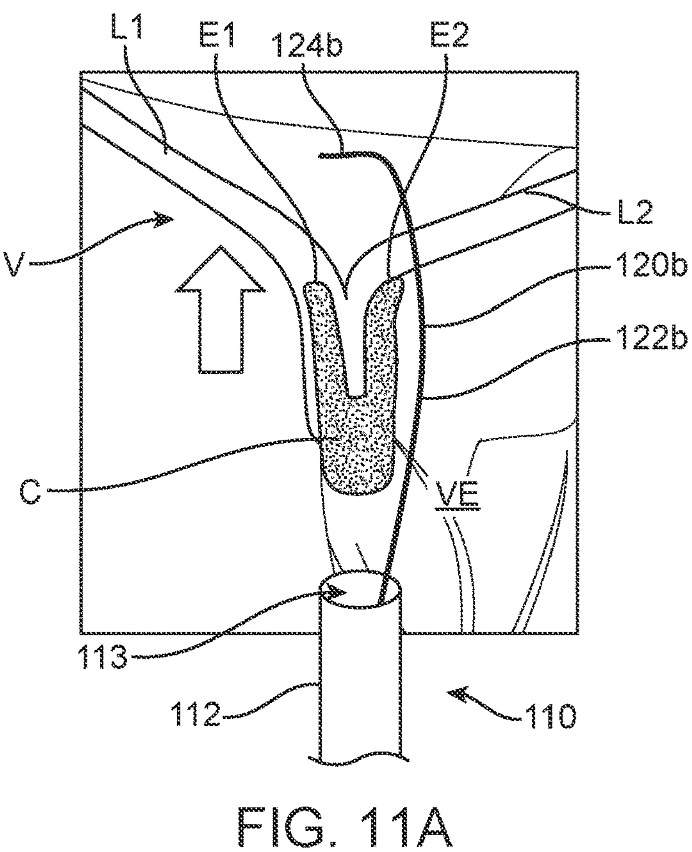
Figure 11B:
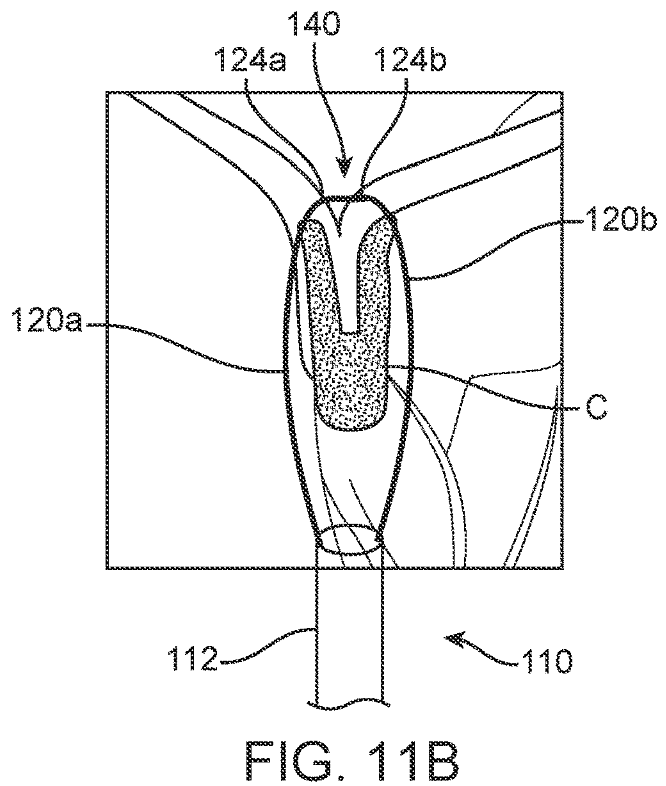
Figure 11C:
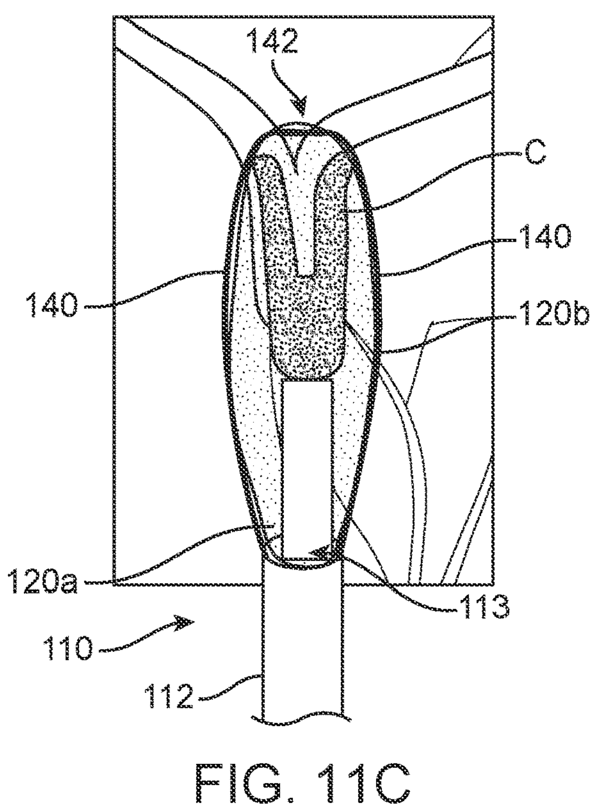
Figure 11D:
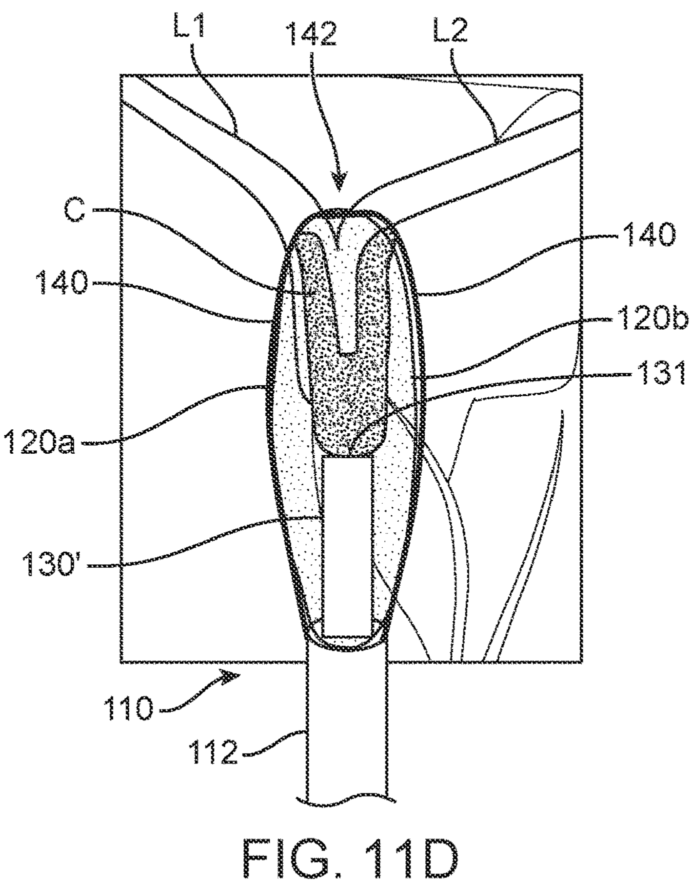

Referring now in addition to FIGS. 11A-11E, the apparatus 110 can also be configured to pull the clip C after delivery of the apparatus 110 via a transapical approach. In this example, the first support 120*a* is inserted through the first opening O1 and the second support is inserted through the second opening O2 from the ventricle VE side such that the distal end portions 124*a*, 124*b* are adjacent each other and also the ends E1, E2 of the clip C. In one example, the distal end portions 124*a*, 124*b* are mechanically hooked together or connected via a magnetic interface. In another example, the distal end portions 124*a*, 124*b* can be connected in the same manner as that disclosed with respect to end portions 24*a*, 24*b* above. After the supports 120*a*, 120*b* are in the position of FIG. 11B, the supports 120*a*, 120*b* are proximally withdrawn toward the outer delivery sheath 112 to pull the clip C off of the leaflets L1, L2, similar to a crowbar. In one example, an alternate wedge assembly or backstop 130' (FIG. 11E) is advanced adjacent the base B prior to proximal withdrawal of the supports 120*a*, 120*b*. The wedge assembly 130' is rigid and coaxially aligned with the outer delivery sheath 112 to serve as a backstop member and support the base B in a stable position as the supports 120*a*, 120*b* apply force to the ends E1, E2. Therefore, in this embodiment, the wedge assembly 130' includes a flat support surface 131 configured to contact the base B. In various embodiments, the supports 120*a*, 120*b* can be provided with the backstop assembly 140*a*, 140*b*, which is configured and operates as disclosed above. Various embodiments, further includes the graspers or supports 120*c*, 120*d*, which can be used to force apart the arms A1, A2 of the clip as is shown in FIG. 11E. Once the clip C is dislodged from the leaflets L1, L2, the supports 120*a-d* can be used to retrieve the clip C and pull the clip into the lumen 113 of the outer delivery sheath 112 for withdrawal of the clip C and apparatus 110 from the patient in the same manner that the apparatus 110 was delivered. It is also envisioned that one or more of supports 120*a*, 120*b*, backstop assemblies 140*a*, 140*b* and/or the wedge assembly 130' can be used to position the clip C prior to dislodging the clip C.

Referring now in addition to FIGS. 12A-12B, which illustrate an alternate apparatus 210 is configured to dislodge the ligation clip C from leaflets L1, L2 via a transapical approach. In one example, the apparatus 210 includes an outer delivery sheath 212 (schematically shown and not to scale) having a lumen 213 in which a support assembly 216 is maintained. The support assembly 216 can include first and second graspers or supports 220*a*, 220*b*. In one example, each grasper 220*a*, 220*b* includes an extension portion 222*a*, 222*b* and a distal end portion 224*a*, 224*b*. The distal end portion 224*a*, 224*b* can include a plurality of barbs 225*a*, 225*b* to better engage the clip C. In one example, the extension portion 222*a*, 222*b* can be constructed of a bar linkage system. In one example, each grasper 220*a*, 220*b* includes four hingedly connected bars (generally referenced as 222*a*, 222*b*) commonly known as a 4-bar linkage mechanism. The linkage mechanism configured to have an open arrangement such that when proximal handles of the graspers 220*a*, 220*b* are positioned away from each other, the distal end portions 224*a*, 224*b* are correspondingly positioned away from each other (FIG. 12A) and when handles 227*a*, 227*b* of the graspers 220*a*, 220*b* are drawn toward each other, the distal end portions 224*a*, 224*b* of the graspers 220*ba*, 220*b* are correspondingly drawn toward each other in a closed arrangement (FIG. 12B).

Use of the apparatus of FIGS. 12A-12B can be summarized as follows. The outer delivery sheath 212 is delivered to the clip C via a transapical approach with the support assembly 216 positioned entirely within the lumen 213 of the outer delivery sheath 212. The graspers 220*a*, 220*b* are then distally advanced so that one distal end portion 224*a*, 224*b* is positioned over each arm A1, A2 of the clip C further into the ventricle VE. Then, the distal end portions 224*a*, 224*b* are engaged with the ends E1, E2 of the arms A1, A2 and drawn proximally to pull the clip C. This step may involve engaging the distal end portions 224*a*, 224*b* to pull the arms A1, A2 away from each other against the bias of the arms A1, A2 to dislodge the clip C from the leaflets L1, L2. Once dislodged from the leaflets L1, L2, the clip C is maintained with the graspers 220*a*, 220*b* and drawn into the lumen 213 of the outer delivery sheath 212 for removal of the apparatus 210 and the clip C in the same manner the apparatus 210 was delivered.

Figure 13A:
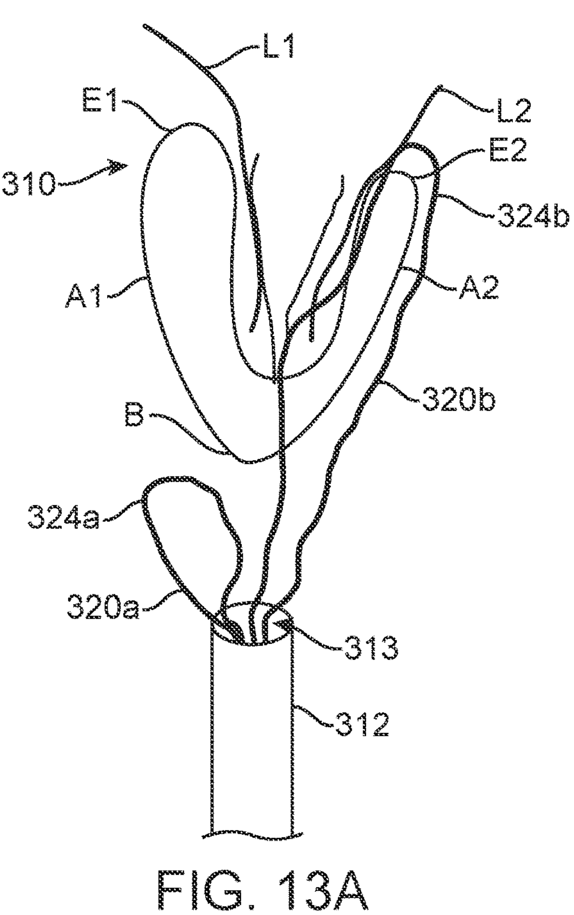
FIGS. 13A-13E are schematic illustrations of an alternate apparatus and method of dislodging and removing the ligation clip from valve leaflets.
Figure 13B:
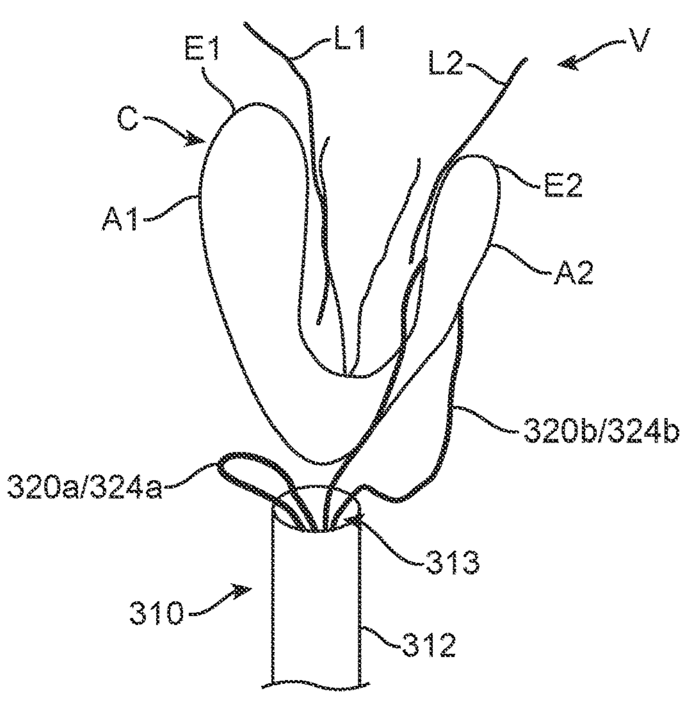
Figure 13C:
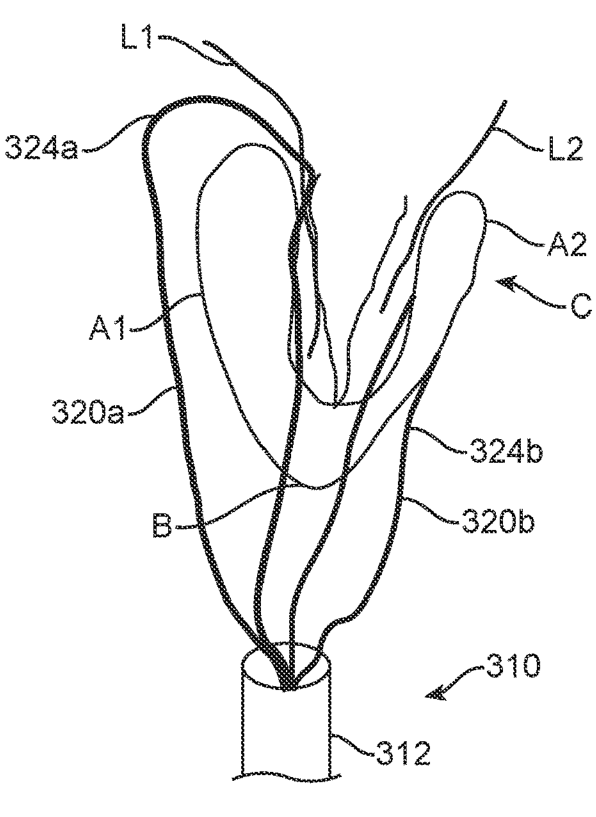
Figure 13D:
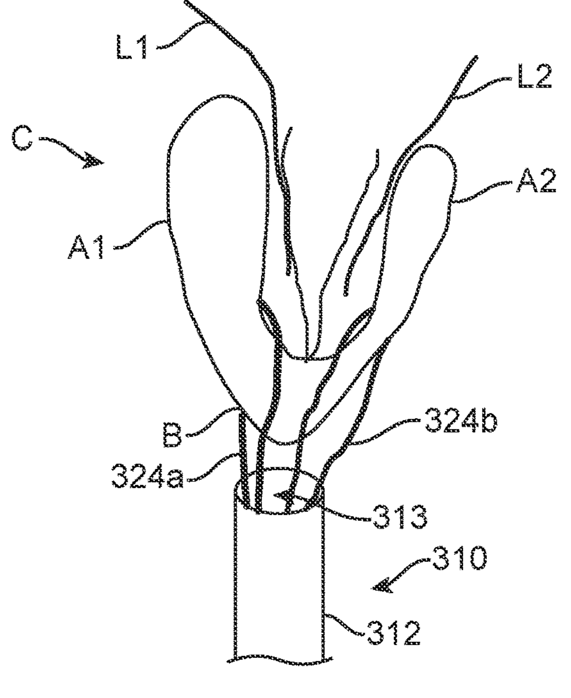
Figure 13E:
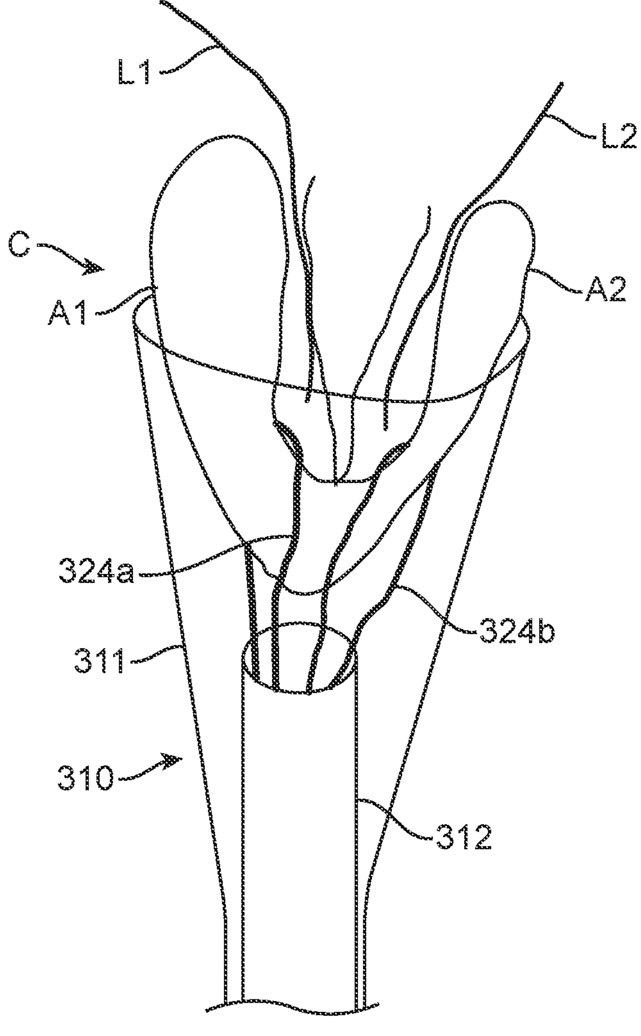
Figure 14A:
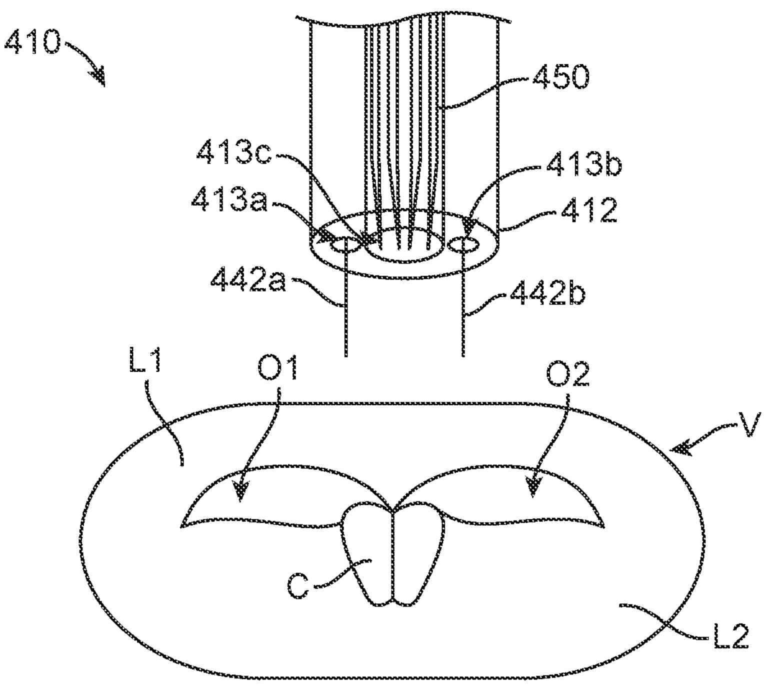
FIGS. 14A-14D are schematic illustrations of an alternate apparatus and method of removing the ligation clip from the valve.
Figure 14B:
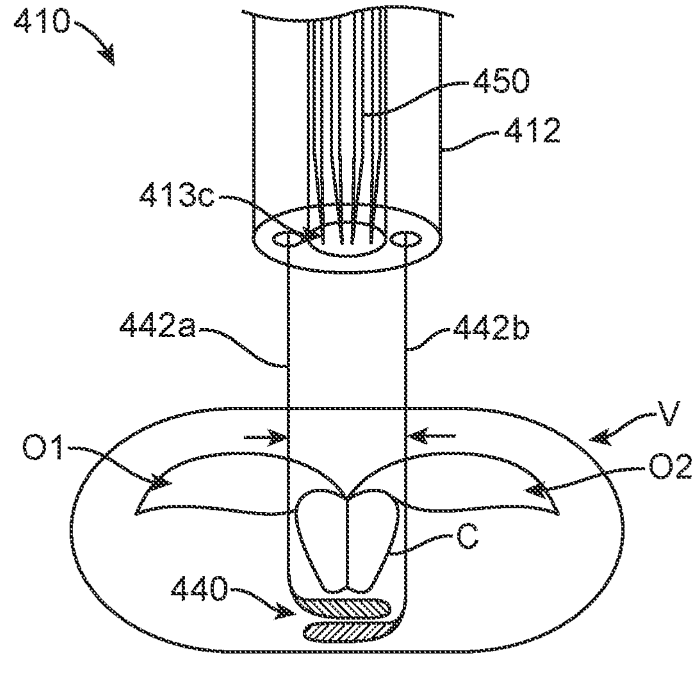
Figure 14C:
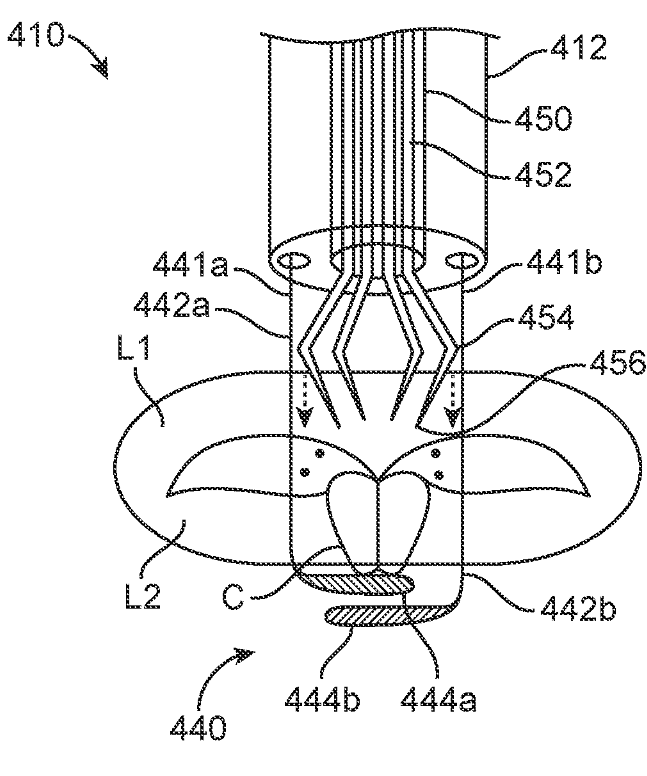
Figure 14D:
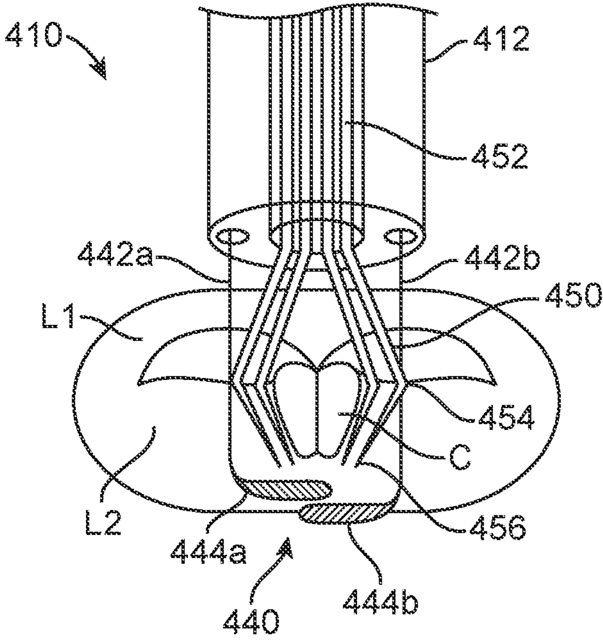

Referring now in addition to FIGS. 13A-13E, which illustrate another apparatus 310 for pulling and dislodging the clip C from the leaflets L1, L2. In this embodiment, the apparatus 310 includes an outer delivery sheath 312 having a lumen 313. The apparatus 310 includes first and second snares 320*a*, 320*b*. In this embodiment, the snares 320*a*, 320*b* can each include a loop 324*a*, 324*b*, which may be formed from wire or the like. Each loop 324*a*, 3224*b* is configured to be looped around one arm A1, A2 of the clip C. In one example of use, the apparatus 310 is delivered to the clip C via transapical approach with the snares 320*a*, 320*b* positioned entirely within the lumen 313 of the outer delivery sheath 312. Once in position adjacent the clip C, each loop 324*a*, 324*b* can be distally advanced out of the lumen 313 and positioned around one respective arm A1, A2 of the clip C. In one example, each loop 324*a*, 324*b* can be positioned between the arms A1, A2 adjacent the base B and the leaflet L1, L2 as is shown in FIG. 13D. Then, the snares 320*a*, 320*b* can be pulled proximally to correspondingly pull the clip C proximally, disengaging the clip C from the leaflets L1, L2. Once disengaged, an outer capture sheath 311 of the apparatus 310 can be advanced over the outer delivery sheath 312 and over the clip C to capture the clip C. In one example, the outer capture sheath 311 can include a shape memory skeleton (e.g. Nitinol) to allow the outer capture sheath 311 to expand around the clip C and then compressively retain the clip C to minimize the apparatus 310 profile during removal of the apparatus 310 and clip C from the patient.

Referring now in addition to FIGS. 14A-14D, which illustrate another apparatus 410 for dislodging the clip C from leaflets L1, L2. In this example, the apparatus 410 includes an outer delivery sheath 412 having respective lumens 413*a*, 413*b* in which a backstop assembly 440 is maintained. In one example, the backstop assembly 440 can include first and second backstop members 441*a*, 441*b*. Each backstop member 441*a*, 441*b* can include an extension portion 442*a*, 442*b* and a distal end portion 444*a*, 444*b*. The distal end portions 444*a*, 444*b* can be angled with respect to the respective extension portion 442*a*, 442*b* (e.g., at an angle of about 90 degrees+/−5 degrees). In one example, each distal end portion 444*a*, 444*b* has a width greater than a diameter of the respective extension portion 442*a*, 442*b*.

The outer delivery sheath 412 also includes a lumen 413*c* in which a plurality of tines 450 are slidably maintained. In one example, three tines 450 are provided. As shown, four tines 450 can be provided in various embodiments. Each tine 450 can include an extension portion 452, an angled portion 454 and a distal tip 456. In various embodiments, the distal tip 456 is pointed to pierce and perforate one respective leaflet L1, L2. As shown, the outer delivery sheath 412 can include separate lumens 413*a*-413*c* (only labeled in FIG. 14A for ease of illustration) for the backstop members 440*a*, 440*b* and the tines 450 but it is envisioned that the outer delivery sheath 412 may only include one lumen in other embodiments of the disclosure. As with prior disclosed embodiments, the backstop members 442*a* 442*b* and at least the angled portion 454 of each tine 450 can be made of a shape memory material so that they can be elongated (i.e. linearly confined) within the outer delivery sheath 412 for delivery and will automatically transition to their respective natural arrangements (FIG. 14D) when released from the confinement of the outer delivery sheath 412. Use of the apparatus 410 can be summarized as follows. The apparatus 410 is delivered to the clip C via a transseptal approach. Then, one support 420*a* can be distally advanced through the first opening O1 and the second support 420*b* can be distally advanced through the second opening O2 so that the respective distal end portions 424*a*, 424*b* are positioned adjacent the base of the clip C (see also, FIG. 1B). In one example, the distal end portions 424*a*, 424*b* are positioned to overlap each other as is shown in FIGS. 12B-12D to form a backstop assembly 440. Then, the tines 450 can be distally advanced from the lumen 413*c* and through the tissue of the leaflets L1, L2. In this example, the leaflets L1, L2 are perforated and a portion of the leaflet tissue is cut away by the tines 450 and is removed along with the clip C. Once the tines 450 are pushed through the leaflets L1, L2 so that the angled portion 452 of the tines 450 grabs the clip C, the backstop members 444*a*, 444*b* and tines 450 are pulled proximally to tear away the perforated portion of the leaflets L1, L2 to pull the clip C, tines 450 and supports 420*a*, 420*b* back into the respective lumens 413*a-c* for removal in the same manner as the apparatus 410 was delivered. Therefore, the clip C will be received and compressively retained within lumen 413*c* with the tines 450. This apparatus 410 is beneficial in instances where there has been calcification of the leaflets L1, L2 at the clip C and the clip may not be easily freed from the leaflets L1, L2 using other apparatuses of the disclosure.

Methods of the disclosure can be generalized as follows. The disclosure includes methods of removing a ligation clip interconnecting two mitral valve leaflets. An example method includes providing a mitral valve having first and second valve leaflets interconnected with a ligation clip; wherein the ligation clip includes a base supporting a first and second retaining arms each having an end opposite the base; wherein the first and second valve leaflets are compressed between the first and second retaining arms. Methods of the disclosure can include physically separating the ligation clip from both of the first and second leaflets with an apparatus configured to dislodge the first and second leaflets from the ligation clip. In some embodiments, the step of physically separating is conducted with an apparatus configured to push the ligation clip distally with respect to the apparatus. In one example, the apparatus includes a tapered wedge member that engages and pushes the ligation clip distally. In one embodiment, the step of physically separating includes deploying first and second supports through first and second openings of the mitral valve on opposing sides of the ligation clip so a distal end portion the first support contacts the base of the ligation clip. Optionally, a backstop member is positioned over the first support. In various embodiments, the first and second supports include a plurality of outwardly extending extensions. In various methods, the step of physically separating is conducted with a first loop positioned around the end of the first arm and a second loop positioned around the end of the second arm. In some methods, the step of physically separating is conducted with an apparatus configured to pull the ligation clip proximally. In various embodiments, the apparatus includes a wedge assembly against which the base of the ligation clip is positioned during the step of physically separating. Methods can optionally include positioning first and second graspers proximate the ends of the first and second arms and pulling the first and second arms to dislodge the ligation clip from the first and second leaflets. In some embodiments, the apparatus includes first support having a loop snare that is deployed from a distal end of the first support and the apparatus further includes a second support is engaged with the loop snare prior to the step of physically separating the ligation clip from both the first and second leaflets.

It should be understood that various aspects disclosed herein may be combined in different combinations than the combinations specifically presented in the description and accompanying drawings. It will be understood that the placement of various components in valve openings O1, O2 can be reversed in alternate examples of disclosed embodiments. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A clip removal apparatus for removing a tissue ligation clip that includes a pair of pivotably coupled tissue engaging elements, the apparatus comprising:

an outer delivery sheath defining a lumen and terminating at a distal end;

a wedge assembly including a tapered wedge member including a blunt tip, the tapered wedge member slidably positioned coaxially with respect to the sheath, the wedge assembly including a delivery arrangement in which the tapered wedge member is positioned within the lumen and a deployed arrangement in which the tapered wedge member is positioned outside the lumen wherein the tapered wedge member is configured to be advanced between the tissue engaging elements of the tissue ligation clip to pivot open the tissue engaging elements to non-destructively remove the tissue ligation clip; and a backstop assembly including a backstop member, the backstop member slidably positioned coaxially with respect to the sheath, the backstop assembly including a delivery arrangement in which the backstop member is positioned within the lumen and a deployed arrangement in which the backstop member is positioned outside the lumen, wherein the backstop member is configured to surround at least a portion of the tissue ligation clip while the tapered wedge member is advanced between the tissue engaging elements of the tissue ligation clip, wherein the backstop member is positioned over a first support, the first support including a loop snare.

2. The apparatus of claim 1, wherein the backstop assembly further includes a support slidably positioned within the sheath; wherein the support has an extension portion connected to a distal end portion, the backstop assembly including a delivery arrangement in which the distal end portion is positioned within the lumen and a deployed arrangement in which the distal end portion is positioned outside of the lumen; wherein the distal end portion of the support includes the backstop member.

3. The apparatus of claim 1, wherein the wedge assembly further includes a wedge support slidably positioned within the sheath, wherein the wedge support has an extension portion connected to a distal end portion, the wedge assembly including a delivery arrangement in which the distal end portion is positioned within the lumen and a deployed arrangement in which the distal end portion is positioned outside of the lumen, and further wherein the distal end portion of the wedge support includes the tapered wedge member.

4. The apparatus of claim 1, wherein the backstop member includes a mesh material.

5. The apparatus of claim 4, wherein the mesh material is shape memory metal mesh.

6. The apparatus of claim 1, wherein the backstop member includes a plurality of outwardly extending extensions.

7. The apparatus of claim 6, wherein the plurality of outwardly extending extensions are flexible.

8. The apparatus of claim 1, further comprising a second support that can be inserted through the loop snare.

9. The apparatus of claim 1, further comprising a first grasper and a second grasper slidably positioned within the sheath, each grasper including a distal end portion; wherein the respective distal end portions of the first and second graspers are angled toward each other when the first and second graspers are positioned at least partially outside of the sheath.

10. A clip removal apparatus for removing a tissue ligation clip that includes a pair of pivotably coupled tissue engaging elements, the apparatus comprising:

an outer delivery sheath defining a lumen and terminating at a distal end;

a shaft slidably disposed within the lumen of the outer delivery sheath;

a wedge assembly including a tapered wedge member including a blunt tip, the wedge assembly including a delivery arrangement in which the tapered wedge member is positioned within a first lumen of the shaft and a deployed arrangement in which the tapered wedge member is positioned outside the first lumen, wherein the tapered wedge member is configured to be advanced between the tissue engaging elements of the tissue ligation clip to pivot open the tissue engaging elements to non-destructively remove the tissue ligation clip;

a backstop assembly including a backstop member, the backstop assembly including a delivery arrangement in which the backstop member is positioned with a second lumen of the shaft a deployed arrangement in which the backstop member is positioned outside the second lumen with at least a portion of the backstop member disposed distal of a distal end of the tapered wedge member with the tapered wedge member and the backstop member in the deployed arrangement such that the backstop member is disposed distal of a distal end of the tissue ligation clip to capture the tissue ligation clip while the tapered wedge member is advanced between the tissue engaging elements of the tissue ligation clip, wherein the backstop assembly further includes a first support slidably positioned within the second lumen in the delivery arrangement, wherein in the deployed arrangement a distal end portion of the support is positioned outside of the second lumen and includes the backstop member, and wherein the first support includes a loop snare at the distal end portion.

11. The apparatus of claim 10, further comprising a second support slidably within a third lumen of the shaft in the delivery arrangement, the second support configured to be inserted through the loop snare with the first support and the second support in the deployed arrangement.

12. The apparatus of claim 10, wherein the backstop member includes a mesh material.

13. The apparatus of claim 12, wherein the mesh material is shape memory metal mesh.

14. The apparatus of claim 10, wherein the backstop member includes a plurality of outwardly extending extensions.

15. The apparatus of claim 14, wherein the plurality of outwardly extending extensions are flexible.

16. The apparatus of claim 10, further comprising a first grasper and a second grasper slidably positioned within the sheath, each grasper including a distal end portion, wherein the respective distal end portions of the first and second graspers are angled toward each other when the first and second graspers are positioned at least partially outside of the sheath.

* * * * *